United States Patent [19]

Möller et al.

[11] Patent Number: 4,824,603

[45] Date of Patent: Apr. 25, 1989

[54] AMPHOTERIC AND ZWITTER-IONIC PHOSPHATE SURFACTANTS

[75] Inventors: Hinrich Möller, Monheim; Ulrich Zeidler, Duesseldorf, both of Fed. Rep. of Germany

[73] Assignee: Henkel Kommanditgesellschaft auf Aktien, Duesseldorf, Fed. Rep. of Germany

[21] Appl. No.: 115,003

[22] Filed: Oct. 28, 1987

[30] Foreign Application Priority Data

Oct. 29, 1986 [DE] Fed. Rep. of Germany ....... 3636750

[51] Int. Cl.$^4$ .......................... C11D 1/88; C11D 1/62; C11D 1/94
[52] U.S. Cl. .................................. 252/545; 252/526; 252/174.16; 252/547; 252/DIG. 7; 252/DIG. 13; 252/DIG. 17; 558/91; 558/92; 558/113; 558/155; 558/158; 558/169
[58] Field of Search .............. 252/174.16, 526, 545, 252/547, DIG. 7, DIG. 13, DIG. 17; 558/91, 92, 113, 155, 158, 169

[56] References Cited

U.S. PATENT DOCUMENTS

| | | | |
|---|---|---|---|
| 3,692,881 | 9/1972 | Stanford et al. | 558/158 |
| 3,925,453 | 12/1975 | Clarke, III | 260/501.12 |
| 4,132,657 | 1/1979 | Verdicchio et al. | 252/32.5 |
| 4,134,970 | 1/1979 | Panke et al. | 424/70 |
| 4,182,687 | 1/1980 | Bartlett | 252/194 |
| 4,208,401 | 6/1980 | Bauman | 424/54 |
| 4,215,064 | 6/1980 | Lindemann et al. | 260/403 |

FOREIGN PATENT DOCUMENTS

62-071528 9/1985 Japan .

OTHER PUBLICATIONS

Chemical Abstracts 98:125401m.

*Primary Examiner*—Paul Lieberman
*Assistant Examiner*—Ronald A. Krasnow
*Attorney, Agent, or Firm*—Ernest G. Szoke; Wayne C. Jaeschke; Henry E. Millson, Jr.

[57] ABSTRACT

Amphoteric and zwitter-ionic phosphate surfactants corresponding to the following formula

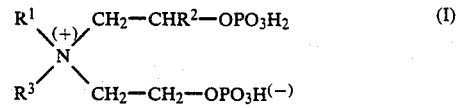

(a) in which $R^1$ is a $C_6$-$C_{22}$ alkyl group, a group $R^4(OC_nH_{2n})_x$—, where n=2 to 4, x=1 to 6, and $R^4$ is a $C_6$-$C_{22}$ alkyl group, or a group $R^5$—CONH(CH$_2$)$_m$, where $R^5$ is a $C_5$-$C_{21}$ group and m=2 to 4; $R^2$ is hydrogen; and $R^3$ is a $C_1$-$C_4$ alkyl group or a group —($C_nH_{2n}O)_x$—H or —($C_nH_{2n}O)_x$—PO$_3$H$_2$, where n=2 to 4 and x=1 to 6, or (b) in which $R^1$ is a $C_1$-$C_4$ alkyl group or a $C_2$-$C_4$ 2-hydroxyalkyl group; $R^2$ is a $C_6$-$C_{22}$ alkyl group; and $R^3$ is as defined above.

to mixtures thereof with correspondingly substituted phosphate surfactants corresponding to formula (I), in which the —PO$_3$H$_2$ group or groups are replaced by hydrogen; and to neutral and basic salts of the foregoing. The invention also relates to processes for the manufacture of the above surfactants, and to their use as skin-compatible washing-active components in body shampoos and hair shampoos.

10 Claims, No Drawings

AMPHOTERIC AND ZWITTER-IONIC PHOSPHATE SURFACTANTS

BACKGROUND OF THE INVENTION

1. Field of the Invention

This invention relates to new amphoteric, zwitterionic, phosphate-group-containing surface-active compounds which contain one tertiary amino group or quaternary ammonium group and two or three phosphate ester groups in the molecule and to a process for the production of these surfactants.

2. Discussion of Related Art

Phosphobetaines containing a quaternary ammonium group and a phosphate ester group have been repeatedly described. For example, U.S. Pat. No. 4,215,064 describes compounds obtainable from reactive chloroalkyl and epoxyalkyl phosphoric acid esters and tertiary amines. Phosphobetaines obtained by reaction of 3-chloro-2-hydroxypropylalkyl ($C_{18}$) dimethylammonium chloride with disodium hydrogen phosphate are known from Chem. Abstr. 98:125401m.

DESCRIPTION OF THE INVENTION

Other than in the operating examples, or where otherwise indicated, all numbers expressing quantities of ingredients or reaction conditions used herein are to be understood as modified in all instances by the term "about".

Amphoteric and zwitter-ionic surfactants containing two or three phosphate ester groups in the molecule have hitherto been unknown. A new simple process has now been found for the production of amphoteric and zwitter-ionic surfactants containing one tertiary amino group or one quaternary ammonium group and two or three phosphate ester groups in the molecule. These new phosphate surfactants are distinguished by valuable properties in terms of practical application.

The present invention relates to amphoteric and zwitter-ionic phosphate surfactants corresponding to the following formula

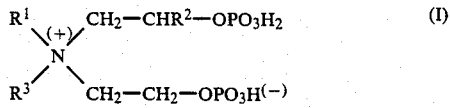

(a) in which $R^1$ is a $C_6$–$C_{22}$ alkyl group, a group $R^4$(O$C_nH_{2n}$)$_x$—, where $n=2$ to 4, $x=1$ to 6, and $R^4$ is a $C_6$–$C_{22}$ alkyl group, or a group $R^5$—CONH(CH$_2$)$_m$—, where $R^5$ is a $C_5$–$C_{21}$ alkyl group and $m=2$ to 4; $R^2$ is hydrogen; and $R^3$ is a $C_1$–$C_4$ alkyl group or a group —($C_nH_{2n}$O)$_x$—H or —($C_nH_{2n}$O)$_x$—$PO_3H_2$, where $n=2$ to 4 and $x=1$ to 6, or (b) in which $R^1$ is a $C_1$–$C_4$ alkyl group or a $C_2$–$C_4$ 2-hydroxyalkyl group; $R^2$ is a $C_6$–$C_{22}$ alkyl group; and $R^3$ is as defined above, to mixtures thereof with correspondingly substituted phosphate surfactants corresponding to formula (I), in which the —$PO_3H_2$ group or groups (when $R^3$ is —($C_nH_{2n}$O)$_x$—$PO_3H_2$, two such groups are present) are replaced by hydrogen; and to neutral and basic salts of the foregoing.

Where $R^3$ is hydrogen, the surfactants are amphoteric surfactants which, below an isoelectric pH value, show predominantly cationic properties and, above that isoelectric point, predominantly anionic properties. If $R^3$ is a substituent, the surfactants are so-called zwitter-ionic surfactants which contain a cationic quaternary ammonium group and anionic phosphate groups.

The surfactants of formula (I) are surface-active because one of the groups $R^1$ or $R^2$ contains a long chain alkyl group. They are distinguished by good foaming power and by high compatibility with anionic, cationic and nonionic surfactants and also with water-soluble polymers differing in their ionicity. Aqueous solutions thereof may be thickened by additions of fatty acid alkanolamides, for example $C_{12}$–$C_{18}$ fatty acid mono- and diethanolamides, and simple salts, such as NaCl or $Na_2SO_4$. In addition, they are highly compatible with the skin and mucous membrane and, accordingly, are particularly suitable for use as a washing-active component in body shampoos and hair shampoos.

Outstanding properties in terms of practical application are shown by those zwitter-ionic surfactants corresponding to formula (I), in which $R^1$ and $R^3$ are each a methyl group and $R^2$ is a $C_8$–$C_{16}$ alkyl group, mixtures thereof with correspondingly substituted surfactants corresponding to formula (I) in which the —$PO_3H_2$ group or groups are replaced by hydrogen, and neutral and basic salts of the surfactants of formula (I).

The amphoteric and zwitter-ionic dihosphate surfactants of the invention are prepared by a simple process. In this process, tertiary bis-(2-hydroxyalkyl)-amines corresponding to the following formula

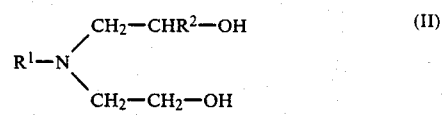

in which $R^1$ and $R^2$ are as defined for formula (I), are phosphatized with polyphosphoric acid, phosphorus oxytrichloride or phosphorus pentoxide and optionally reacted with alkylating agents of the formula $R^3$Cl, $R^3$Br, $R_2^3SO_4$, where $R^3$ is a $C_1$–$C_4$ alkyl group, or with $x$ moles of an alkylene oxide having the formula $C_2H_{2n}O$, under conditions which lead to quaternization of the tertiary amine.

Suitable bis-(2-hydroxyalkyl)-amines corresponding to formula (II) are, for example, the adducts of 2 moles ethylene oxide with $C_6$–$C_{22}$ fatty amines, the condensates of $C_6$–$C_{22}$ fatty acids with 1 mole N,N-bis-(2-hydroxyethyl)-alkylene-($C_2$–$C_4$)-diamines and the condensates of 2-hydroxyethylalkyl-($C_1$–$C_4$)-amines with $C_8$–$C_{24}$ α-epoxyalkanes.

The phosphatization step and the optional quaternization step may be carried out in any order. Accordingly, it is also possible initially to convert the bis-(2-hydroxyalkyl)-amine corresponding to formula (II) into a quaternary ammonium compound corresponding to the following formula

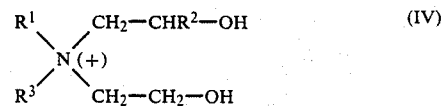

by reaction with an alkylating agent or with a $C_2$–$C_4$ alkylene oxide and then to phosphatize the quaternary ammonium compound (IV) with polyphosphoric acid, phosphorus oxytrichloride or phosphorus pentoxide in excess.

The quaternization with the alkylating agents mentioned or with an alkylene oxide may be carried out in aqueous or aqueous-alcoholic solution by any of the standard methods known for this purpose. For alkylation with $R^3Cl$, $R^3Br$ or $R_2{}^3SO_4$, the free tertiary amines are used; the quaternization with alkylene oxides is preferably carried out in neutral or mildly acidic, aqueous or aqueous-alcoholic solution.

The phosphatization of the bis-(2-hydroxyalkyl)-amines corresponding to formula (II) is carried out by reaction with polyphosphoric acid, diphosphoric acid, phosphorus pentoxide or phosphorus oxychloride using any of the standard methods known for this purpose.

Polyphosphoric acid of high $P_2O_5$ content is preferably used. It is preferably used in excess, a molar ratio of 1.5 to 3 and preferably 2 moles of $P_2O_5$ to 1 mole of the bis-(2-hydroxyalkyl)amine having proved to be very suitable. The reaction is carried out in the absence of a solvent at temperatures of from 40 to 150° C. The phosphatization with $POCl_3$ is preferably carried out at temperatures of from 0° to 50° C., preferably in a solvent, such as tetrahydrofuran or diethylene glycol dimethylether, using an auxiliary base, such as pyridine or triethanolamine for example, to bind the hydrochloric acid formed.

Phosphatization can also be carried out with orthophosphoric acid in the absence of a solvent and at temperatures above 150° C.

The phosphatization of the quaternary ammonium compounds corresponding to formula (IV) is preferably carried out in an organic, water-miscible solvent free from hydroxyl groups, for example in tetrahydrofuran, dioxane, 1,2-dimethoxyethane or diethylene glycol dimethylether. The highest degrees of phosphatization are obtained in this case.

Another possible method of preparing the zwitterionic phosphate surfactants corresponding to formula (I), preferably those in which $R^1$ is a $C_1$–$C_4$ alkyl group and $R^2$ is a $C_6$–$C_{22}$ alkyl group, comprises initially phosphatizing tertiary hydroxyalkylamines corresponding to the following formula

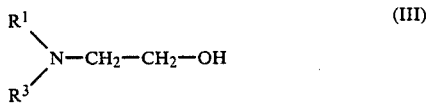

(III)

with polyphosphoric acid, $POCl_3$ or $P_2O_5$, reacting the product thus formed with a long-chain epoxide corresponding to the formula

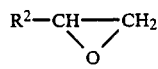

and then rephosphatizing the product of this reaction. The phosphatization of the tertiary hydroxyalkylamine corresponding to formula (III) need only be carried out with 0.05 to 0.2 mole P of the phosphatizing reagent per mole of the hydroxyalkylamine, the phosphatization of the reaction product with the epoxide preferably being carried out with an excess of the phosphatizing agent. It has proved to be effective, for example, to use in all about 2 moles $P_2O_5$, preferably in the form of polyphosphoric acid, to 1 mole of the reaction product.

Mixtures of the diphosphate surfactants of formula (I) according to the invention with correspondingly substituted monophosphate surfactants corresponding to formula (I), in which the group $-OPO_3H_2$ is replaced by $-OH$, are obtained by the process of the invention. This is due to the fact that complete phosphatization of all the hydroxyl groups is not achieved under the disclosed reaction conditions. If the degree of phosphatization is regarded as that percentage of the hydroxyl groups in the starting product which is converted into an $-OPO_3H_2-$ group, the diphosphate surfactants of formula (I) are always formed for a degree of phosphatization above 0.5.

The degree of phosphatization can be controlled by using an excess of the phosphatizing agent. The degree of phosphatization can be estimated as follows from the analytical data of the phosphatization product:

$$\text{degree of phosphatization} = \frac{P(\text{total}) - P(\text{inorg.})}{1/n P(\text{total})}$$

The values for P(total) (=% by weight total phosphorus) and for P(inorg.) (=% by weight inorganically bound phosphorus) may be determined by known analytical methods. n is the molar quantity of phosphorus used per hydroxyl group. The reaction mixtures are worked up after the phosphatization by addition of water and heating to 80° to 100° C. until the polyphosphate and diphosphate structures are hydrolyzed. This reaction is over after 30 to 60 minutes. Alkali metal hydroxide or alkali metal carbonate is then added in the quantity required for formatilon of the desired salt. Potassium hydroxide solution is used to prepare the corresponding potassium salts and aqueous ammonia solution to prepare ammonium salts. It is also possible to prepare alkanolamine salts, for example by addition of monoethanolamine, diethanolamine, triethanolamine, isopropanolamine, or other amine salts, for example with morpholine, piperidine and other amines.

Inorganic orthophosphate may be precipitated in the form of the sparingly soluble Ca salt by addition of relatively small quantities of calcium hydroxide and thus removed from the product.

The following Examples are intended to illustrate the invention without limiting it in any way.

EXAMPLES

1. Phosphatization of 2-hydroxyethyl-2-hydroxyhexadecylmethylamine 39.4 g (0.125 mole) of 2-hydroxyethyl-2-hydroxyhexadecylmethylamine (from 2-methylaminoethanol and α-hexadecene oxide) having an amine number of 184 were stirred at 20° C. with 42.2 g (0.25 mole $P_2O_5$) of polyphosphoric acid (84% by weight $P_2O_5$) and heated to 150° C. in 15 minutes. After cooling to 80° C., the reaction mixture was taken up in approximately 350 g of water and neutralized with 50% by weight aqueous sodium hydroxide. Undissolved secondary products were separated off by filtration. The degree of phosphatization was 0.53.

2. 2-hydroxyethyl-2-hydroxyhexadecyl dimethylammonium phosphate 200 g of the solution of Example 1 were reacted with 20 g of methyl chloride in an autoclave at 100° C./5 bar $N_2$ pressure. The reaction was over after 3.5 hours. The solution obtained was concentrated to dryness under reduced pressure, a colorless wax-like substance being obtained. This substance showed the following analytical data:

H₂O: 3.2% by weight
Cl (−) 9.1% by weight
Degree of phosphatization: 0.53

3. Phosphatization of dimethyl-2-hydroxyethyl-2-hydroxy-hexadecylammonium chloride 36.6 g (0.1 mole) of dimethyl-2-hydroxyethyl-2-hydroxyhexadecylammonium chloride were added with stirring at 80° C. to a mixture of 33.8 g (0.2 mole $P_2O_5$) or polyphosphoric acid (84% by weight $P_2O_5$) and 200 ml of diethylene glycol dimethylether. The reaction mixture was heated with stirring for 5 hours to 100° C., becoming homogeneous in the process. After removal of the solvent by distillation under reduced pressure, 400 ml water were added to the residue, followed by heating to boiling temperature. After cooling to 50° C., the mixture was adjusted to pH 7 with 50% aqueous sodium hydroxide and filtered hot with active carbon. The solution showed the following analytical data:
P(total): 14.9% by weight
P(inorg.): 8.4% by weight $$\text{Degree of phosphatization} = \frac{P(total) - P(inorg.) \times 2}{P(total)} = 0.87$$

4. Fatty acyl-($C_{12}$–$C_{14}$-aminopropyldi-(2-hydroxyethyl)-methylammonium phosphate

4.1 First stage
N,N-bis-(2-hydroxyethyl)-N'-fatty acyl-($C_{12}$–$C_{14}$)-1,3 propylenediamine was first prepared from $C_{12}$–$C_{14}$ fatty acid (70:30) and N,N-bis-(2-hydroxyethyl)-1,3-propylenediamine in toluene with azeotropic removal of the water of condensation.

4.2 Phosphatization
88 g (0.25 mole) of the aminoamide of 4.1 were added to 84.4 g (0.5 mole $P_2O_5$) of polyphosphoric acid (84% by weight $P_2O_5$) with stirring at 90 to 100° C. in the absence of water. The mixture was heated to 150° C. in 15 minutes and stirred at that temperature for 30 minutes. After cooling to 80° C., the reaction mixture was stirred into 300 g of water, adjusted to pH 7 with 50% aqueous sodium hydroxide and separated off from a little undissolved secondary product by filtration.

4.3 Quaternization
200 g of the solution of 4.2 (0.093 mole) were reacted with 20 g (0.4 mole) of methyl chloride in an autoclave at 100° C./5 bar $N_2$ pressure. The reaction was over after 3.5 hours. The vigorously foaming solution was concentrated to dryness under reduced pressure, a colorless wax-like substance being obtained. This substance showed the following analytical data:
P(total): 13% by weight
P(inorg.): 8.9% by weight
H₂O: 5.5% by weight
Cl⁻: 7.1% by weight $$\text{Degree of phosphatization} = \frac{P(total) - P(inorg.) \times 2}{P(total)} = 0.63$$

5. Phosphatized dimethyl-2-hydroxyethyl-2-hydroxyhexadecylammonium phosphate 44.6 g (0.5 mole) of 2-dimethylaminoethanol were added with stirring to 20 g (0.118 mole $P_2O_5$) of polyphosphoric acid (84% by weight $P_2O_5$). After the exothermic reaction had abated, the reaction mixture was heated for 2 hours to boiling temperature. After cooling to 80° C., 120 g (0.5 mole) of 1,2-epoxyhexadecane were stirred in and the temperature slowly increased to 100° C. On completion of the exothermic reaction occuring, the reaction mixture was heated for 1 hour at 100° C. and for 0.5 hour at 135° C. and, after the addition of 100 ml of diethylene glycol dimethylether, was heated for another hour to boiling temperature. The yellow-brown solution cooled to 100° C. was introduced into 149 g (0.88 mole $P_2O_5$) of polyphosphoric acid which had been previously heated to 80° C. and the mixture stirred for 2 hours at 130° C. The solvent was then distilled off under reduced pressure, the residue taken up in 500 ml of water, the solution heated for 0.5 hour to boiling temperature and, after neutralization with sodium hydroxide (50%), concentrated by evaporation to dryness. A grey-white solid product was obtained.
P(total): 16.9% by weight
P(inorg.): 11.2% by weight
Degree of phosphatization: 0.68

The following compounds were prepared in accordance with Examples 1 to 5:

6. Phosphatized dimethyl-2-hydroxyethyl-2-hydroxytetradecylammonium chloride (in accordance with Example 3)

Degree of phosphatization: 0.89

7. Phosphatized bis-2-hydroxyethyl-3-($C_{12}$–$C_{14}$-fatty acid amido)-propylmethylammonium chloride (in accordance with Example 3)

Degree of phosphatization: 0.98

8. Phosphatized $C_{12}$–$C_{14}$-alkylpoly(3,6)oxyethyl-bis-(2-hydroxyethyl)-methylammonium chloride Starting out from a $C_{12}$–$C_{14}$-alkylpoly(3,6)glycol ether sulfate, Na salt, the $C_{12}$–$C_{14}$ alkylpoly(3,6)oxyethyl-bis-(2-hydroxyethyl)-amine was prepared by alkylation of diethanolamine. It was quaternized with methyl chloride and the quaternary ammonium salt phosphatized in accordance with Example 3.

9. Phosphatized cocosalkyl-tris-(2-hydroxyethyl)-ammonium chloride

Cocosalkyl-bis-(2-hydroxyethyl)-amine hydrochloride was quaternized with ethylene oxide in an aqueous-alcoholic solution (2-propanol: H₂O=1:1) at 85° C. The quaternary ammonium chloride was phosphatized with polyphosphoric acid (3 moles $P_2O_5$ per mole) in accordance with Example 2. Degree of phosphatization: 0.85.

10. Phosphatized 2-dodecyloxyethyl tris-2-hydroxyethyl-ammonium chloride

Starting from 2-dodecyloxyethyl sulfate, Na salt, 2-dodecyloxyethyl-bis-(2-hydroxyethyl)-amine was prepared by alkylation of diethanolamine, converted into the hydrochloride and quaternized with ethylene oxide in aqueous alcoholic solution. Phosphatization was carried out with polyphosphoric acid (3 moles $P_2O_5$ per mole). Degree of phosphatization: 0.93.

We claim:
1. Amphoteric and zwitter-ionic phosphate surfactants of the formula:

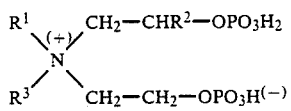

(a) in which $R^1$ is a group $R^4(OC_nH_{2n})_x-$, where n=2 to 4, x=1 to 6, and $R^4$ is a $C_6$-$C_{22}$ alkyl group, or a group $R^5$—$CONH(CH_2)_m$, where $R^5$ is a $C_5$-$C_{21}$ alkyl group and m=2 to 4; $R^2$ is hydrogen, and $R^3$ is a $C_1$-$C_4$ alkyl group, or a group —$(C_nH_{2n}O)_x$—H or —$(C_nH_{2n}O)_x$—$PO_3H_2$, where n=2 to 4 and x=1 to 6, or (b) in which $R^1$ is a $C_1$-$C_4$ alkyl group or a $C_2$-$C_4$ 2-hydroxyalkyl group; $R^2$ is a $C_6$-$C_{22}$ alkyl group; and $R^3$ is as defined above;

mixtures thereof with correspondingly substituted surfactants of formula (I) in which the —$PO_3H_2$ group or groups are replaced by hydrogen; and neutral and basic salts of the foregoing phosphate surfactants.

2. The surfactant of claim 1 wherein $R^1$ and $R^3$ are each methyl groups, and $R^2$ is a $C_8$-$C_{16}$ alkyl group; mixtures thereof with a corresponding substituted phosphate surfactant of formula (I) in which the —$PO_3H_2$ group or groups are replaced by hydrogen; and neutral and basic salts of the foregoing.

3. A process for the production of amphoteric and zwitter-ionic phosphate surfactants of the formula:

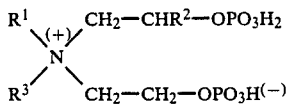

(a) in which $R^1$ is a group $R^4(OC_nH_{2n})_x-$, where n=2 to 4, x=1 to 6, and $R^4$ is a $C_6$-$C_{22}$ alkyl group, or a group $R^5$—$CONH(CH_2)_m$, where $R^5$ is a $C_5$-$C_{21}$ alkyl group and m=2 to 4; $R^2$ is hydrogen; and $R^3$ is a $C_1$-$C_4$ alkyl group, or a group —$(C_nH_{2n}O)_x$— or —$(C_nH_{2n}O)_x$—$PO_3H_2$, where n=2 to 4 and x=1 to 6, or (b) in which $R^1$ is a $C_1$-$C_4$ alkyl group or a $C_2$-$C_4$ 2-hydroxyalkyl group; $R^2$ is a $C_6$-$C_{22}$ alkyl group; and $R^3$ is as defined above;

comprising the steps of:

(A) phosphatizing a tertiary bis-(2-hydroxyalkyl)-amine of the formula:

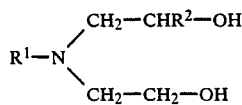

with polyphosphoric acid, $POCl_3$ or $P_2O_5$, and (B) quaternizing the resulting phosphatized amine with an alkylating agent of the formula $R^3Cl$, $R^3Br$, $R^2SO_4$, where $R^3$ is a $C_1$-$C_4$ alkyl group, or with x moles of an alkylene oxide corresponding to the formula $C_nH_{2n}O$, wherein either of steps (A) or (B) can be carried out first.

4. The process of claim 3 wherein step (A) is carried out with polyphosphoric acid in the absence of a solvent at a temperature in the range of from about 40° to about 140° C.

5. The process of claim 4 wherein the polyphosphoric acid has a high $P_2O_5$ content and is used in a molar ratio of from about 1.5 to about 3 moles of $P_2O_5$ per mole of amine of formula (II).

6. The process of claim 3 wherein step (A) is carried out with $POCl_3$ at a temperature in the range of from about 0° to about 50° C.

7. The process of claim 6 wherein the reaction of $POCl_3$ is carried out in an organic solvent in the presence of a base to bind hydrochloric acid formed in the process.

8. The process of claim 3 wherein step (B) is carried out in a neutral or mildly acidic aqueous or aqueous-alcoholic solution.

9. A process for the preparation of amphoteric and zwitter-ionic surfactants of the formula:

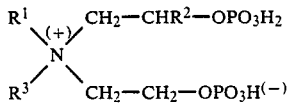

(a) in which $R^1$ is a group $R^4(OC_nH_{2n})_x-$, where n=2 to 4, x=1 to 6, and $R^4$ is a $C_6$-$C_{22}$ alkyl group, or a group $R^5$—$CONH(CH_2)_m$, where $R^5$ is a $C_5$-$C_{21}$ alkyl group and m=2 to 4; $R^2$ is hydrogen; and $R^3$ is a $C_1$-$C_4$ alkyl group, or a group —$(C_nH_{2n}O)_x$—H or —$(C_nH_{2n}O)_x$—$PO_3H_2$, where n=2 to 4 and x=1 to 6, or (b) in which $R^1$ is a $C^1$-$C_4$ alkyl group or a $C_2$-$C_4$ 2-hydroxyalkyl group; $R^2$ is a $C_6$-$C_{22}$ alkyl group; and $R^3$ is as defined above;

comprising the steps of:

(A) phosphatizing a tertiary hydroxyalkylamine of the formula:

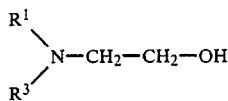

with polyphosphoric acid, $POCl_3$ or $P_2O_5$, (B) reacting an epoxide corresponding to the formula

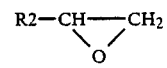

and the product of step (A), and (C) phosphatizing the product of step (B) with polyphosphoric acid, $POCl_3$, or $P_2O_5$.

10. In a body shampoo or hair shampoo, the improvement comprising the presence therein of a washing-active quantity of the surfactant of claim 1.

* * * * *

UNITED STATES PATENT AND TRADEMARK OFFICE
CERTIFICATE OF CORRECTION

PATENT NO. : 4,824,603
DATED : April 25, 1989
INVENTOR(S) : Hinrich Moeller et al.

It is certified that error appears in the above-identified patent and that said Letters Patent is hereby corrected as shown below:

In Claim 3, at Col. 7, lines 41-42, for "$(C_nH_{2n}O)_x$", read --$(C_nH_{2n}O)_x$-H--.

Signed and Sealed this

Twentieth Day of March, 1990

*Attest:*

JEFFREY M. SAMUELS

*Attesting Officer*     *Acting Commissioner of Patents and Trademarks*